United States Patent
Yi et al.

(10) Patent No.: US 12,079,988 B2
(45) Date of Patent: Sep. 3, 2024

(54) MEDICAL IMAGE RECONSTRUCTION APPARATUS AND METHOD FOR SCREENING FOR PLURALITY OF TYPES OF LUNG DISEASES

(71) Applicant: Coreline Soft Co., Ltd., Seoul (KR)

(72) Inventors: Jaeyoun Yi, Seoul (KR); Donghoon Yu, Gimpo-si (KR); Yongjin Chang, Incheon (KR); Sol A Seo, Seoul (KR); Sunggoo Kwon, Guri-Si (KR)

(73) Assignee: Coreline Soft Co., Ltd., Seoul (KR)

( * ) Notice: Subject to any disclaimer, the term of this patent is extended or adjusted under 35 U.S.C. 154(b) by 361 days.

(21) Appl. No.: 17/538,625

(22) Filed: Nov. 30, 2021

(65) Prior Publication Data

US 2022/0172353 A1 Jun. 2, 2022

(30) Foreign Application Priority Data

Nov. 30, 2020 (KR) .................. 10-2020-0164449

(51) Int. Cl.
*G06T 7/00* (2017.01)
*G06N 3/08* (2023.01)
*G16H 30/40* (2018.01)

(52) U.S. Cl.
CPC ............ *G06T 7/0012* (2013.01); *G06N 3/08* (2013.01); *G16H 30/40* (2018.01); *G06T 2207/20081* (2013.01); *G06T 2207/20084* (2013.01); *G06T 2207/30061* (2013.01)

(58) Field of Classification Search
None
See application file for complete search history.

(56) References Cited

U.S. PATENT DOCUMENTS

| | | |
|---|---|---|
| 7,817,835 B2 | 10/2010 | Fan et al. |
| 9,691,167 B1 | 6/2017 | Frenkel et al. |
| 9,773,305 B2 | 9/2017 | Lee et al. |
| 10,368,809 B2 | 8/2019 | Kim et al. |

(Continued)

FOREIGN PATENT DOCUMENTS

| | | |
|---|---|---|
| KR | 10-2007-0098647 A | 10/2007 |
| KR | 10-1241060 B1 | 3/2013 |

(Continued)

*Primary Examiner* — Leon Flores
(74) *Attorney, Agent, or Firm* — United One Law Group LLC; Kongsik Kim; Jhongwoo Peck

(57) ABSTRACT

Disclosed herein is a medical image reconstruction apparatus for reconstructing a medical image to assist the reading of a medical image. The medical image reconstruction apparatus includes a computing system, which includes: a receiver interface configured to receive a first medical image to which a first reconstruction parameter adapted to diagnose or analyze a first type of lesion is applied; and at least one processor configured to generate a second reconstruction parameter to be applied to the first medical image in response to a diagnosis order for the diagnosis or analysis of a second type of lesion. The at least one processor provides the second reconfiguration parameter to a user via a user interface, or generates a second medical image for the diagnose or analysis of the second type of lesion by executing the second reconstruction parameter on the first medical image and provides the second medical image to the user.

20 Claims, 8 Drawing Sheets

(56) References Cited

U.S. PATENT DOCUMENTS

| | | |
|---|---|---|
| 10,383,592 B2 | 8/2019 | Park |
| 10,565,477 B2 | 2/2020 | Hsieh et al. |
| 2015/0036903 A1* | 2/2015 | Jerebko ................ G06T 11/006 |
| | | 382/131 |
| 2019/0369191 A1 | 12/2019 | Gong et al. |
| 2020/0294284 A1 | 9/2020 | Adler et al. |
| 2020/0311490 A1 | 10/2020 | Lee et al. |
| 2020/0335201 A1 | 10/2020 | Ionasec et al. |

FOREIGN PATENT DOCUMENTS

| | | |
|---|---|---|
| KR | 10-2014-0091176 A | 7/2014 |
| KR | 10-2016-0012758 A | 2/2016 |
| KR | 10-1910822 B1 | 10/2018 |
| KR | 10-1923962 B1 | 11/2018 |
| KR | 10-2019-0002960 A | 1/2019 |
| KR | 10-1943011 B1 | 1/2019 |
| KR | 10-2070427 B1 | 1/2020 |

* cited by examiner

MEDICAL IMAGE RECONSTRUCTION APPARATUS AND METHOD FOR SCREENING FOR PLURALITY OF TYPES OF LUNG DISEASES

CROSS-REFERENCE TO RELATED APPLICATION

This application claims priority to Korean Patent Application No. 10-2020-0164449 filed on Nov. 30, 2020, which is incorporated herein by reference in its entirety.

TECHNICAL FIELD

The present invention relates to an apparatus and method that assist the reading of a medical image of a subject. More particularly, the present invention relates to a computing system that assists the reading of a medical image using an analysis result of a medical artificial neural network, and software that is executed in the computing system.

RELATED ART

Currently, medical images such as computed tomography (CT) images are widely used to analyze lesions and use analysis results for diagnosis. For example, chest CT images are frequently used for reading because they allow readers to observe abnormalities in parts of the human body such as the lungs, the bronchi, and the heart.

As X-ray CT images are used for various applications such as cancer screening, efforts are made to minimize ab effect on the human body by reducing the dose of a clinical CT scan.

Many technologies are being developed to improve the image quality of low-dose CT. In general, in order to reduce noise and improve image quality even at a low dose, artificial neural network (ANN) technology is recently applied to low-dose CT.

In U.S. Patent Application Publication No. US 2020/0335201 entitled "Method for Setting a Medical Imaging Protocol, System for Setting a Medical Instrument, Computer Program and Computer-Readable Medium," preliminary diagnosis/findings are derived from interviews between a patient and a doctor, and an artificial neural network proposes parameters and protocols necessary for imaging, reconstruction, and recording based on the preliminary diagnosis. After the proposed parameters and protocols have been executed without change or parameters and protocols modified by medical staff have been executed, lesions detected by image analysis are compared with the preliminary diagnosis/findings, the results of the comparison are fed back to the artificial neural network, and the artificial neural network learns the results.

In U.S. Patent Application Publication No. US 2020/0311490 entitled "Apparatus and Method for Sinogram Restoration in Computed Tomography (CT) Using Adaptive Filtering with Deep Learning (DL)," parameters necessary for reconstruction are proposed using deep learning and adaptive filtering in order to reduce noise in a medical image and improve image quality in general CT.

U.S. Pat. No. 10,565,477 entitled "Deep Learning Medical Systems and Methods for Image Reconstruction and Quality Evaluation" discloses an example of applying a deep learning technique for the purpose of the reconstruction and quality evaluation of a medical image. Examples of deep learning include a convolutional neural network (CNN), a recurrent neural network (RNN), and a generative adversarial network (GAN).

U.S. Patent Application Publication No. US 2019/0369191 entitled "MRI Reconstruction Using Deep Learning, Generative Adversarial Network and Acquisition Signal Model" discloses an example of reconstructing a magnetic resonance imaging (MRI) image using a generative adversarial neural network (GAN).

Recent studies have increasingly attempted to use generative adversarial neural networks to improve medical image quality. However, since the generative adversarial neural network does not completely depend on an original medical image and generates a new result image, there are frequent cases where the generated result image does not fully maintain the clinical characteristics of the original medical image.

Accordingly, U.S. Patent Application Publication No. US 2020/0294284 entitled "Posterior Image Sampling Using Statistical Learning Model" discloses an attempt that is made to represent uncertainty or error in a reconstructed image by using a conditional generative adversarial neural network (CGAN) instead of a simple GAN.

However, even according to the above related art documents, the reconstruction of a medical image still has a limitation in that a medical image cannot be reconstructed again after being reconstructed in a medical imaging device or modality.

Furthermore, although the GAN (generative adversarial neural network) generates a medical image having excellent quality for the human eye, the possibility that the clinical characteristics of an original medical image are not be maintained without change cannot be ignored.

SUMMARY

As to recent medical images such as CT or MRI images, a series of medical images is acquired through a single acquisition process, and the series of medical images is not limited to a single type of lesion but may also be used to detect various types of lesions. For example, for the lungs, a lung nodule as well as chronic obstructive pulmonary disease (COPD) may be diagnosed, emphysema may be diagnosed, and/or chronic bronchitis and/or an airway-related disease may also be diagnosed. In addition, coronary artery calcification (CAC) scoring may be analyzed in a chest CT image in addition to lung disease.

In the related arts, a medical image is generated as a medical image that can be clinically interpreted by medical staff through a medical image reconstruction process from a set of signals received from a medical imaging device. There are independent reconstruction parameters and/or reconstruction protocols adapted to diagnose respective multiple lesions from original data (a set of signals) or an original medical image.

In the related arts, when individual reconstruction protocols are applied to original data or an original medical image, individual medical images capable of diagnosing a plurality of lesions, respectively, can be generated from the one original medical image. However, when a reconstruction process has been finished and a session has been completed in a medical imaging device, the original medical image is lost and a reconstruction process cannot be performed any longer.

The aforementioned related arts, i.e., U.S. Patent Application Publication No. US 2020/0335201 entitled "Method for Setting a Medical Imaging Protocol, System for Setting a Medical Instrument, Computer Program and Computer-Readable Medium," U.S. Patent Application Publication No. US 2020/0311490 entitled "Apparatus and Method for Sinogram Restoration in Computed Tomography (CT) Using Adaptive Filtering with Deep Learning (DL)," U.S. Pat. No. 10,565,477 entitled "Deep Learning Medical Systems and Methods for Image Reconstruction and Quality Evaluation," U.S. Patent Application Publication No. US 2019/0369191 entitled "MRI Reconstruction Using Deep Learning, Generative Adversarial Network and Acquisition Signal Model," and U.S. Patent Application Publication No. US 2020/0294284 entitled "Posterior Image Sampling Using Statistical Learning Model" are all directed to technology for improving the process of reconstructing a medical image in a medical imaging device by using an artificial neural network. However, even according to these related art documents, after a reconstruction process has been finished, it is impossible to obtain a medical image, to which another reconstruction parameter and/or reconstruction protocol is applied, from the same original medical image.

However, in society today, as the types of diseases become more diversified and complicated and situations requiring the analysis of a medical image also become diversified, cases requiring the diagnosis of additional disease or lesion are becoming more frequent. Since performing new medical imaging every time exposes a patient to a high radiation dose, there is a demand for a method that can reuse an existing medical image without performing new medical imaging as much as possible.

The present invention is an invention contrived to deal with the limitations of the related arts and a new demand, and an object of the present invention is to propose a new reconstruction parameter and/or reconstruction protocol suitable for diagnosing/analyzing an additional disease or lesion without damaging the clinical characteristics of an original medical image from a medical image received after a reconstruction process has already been completed in a medical imaging device, and to propose a medical image reconstruction apparatus capable of reconstructing a new medical image based on the new reconstruction parameter and/or reconstruction protocol and diagnosing/analyzing the additional disease or lesion.

An object of the present invention is to propose a medical image reconstruction apparatus and method capable of diagnosing/analyzing an additional disease or lesion from a currently given medical image by executing medical image processing via software, independently from a medical imaging device.

An object of the present invention is to provide a technique for conversion between medical image reconstruction parameters (protocols) capable of diagnosing/analyzing an additional disease or lesion from the same original medical image by using the training/learning and inference of an artificial neural network. In this case, the conversion between medical image reconstruction parameters (protocols) is performed independently of a medical imaging device, and can be performed even in an environment in which information about an original medical image cannot be received from a medical imaging device because the medical imaging device finishes a medical image reconstruction process.

According to an aspect of the present invention, there is provided a medical image reconstruction apparatus for reconstructing a medical image to assist reading of a medical image, the medical image reconstruction apparatus including a computing system. The computing system includes: a receiver interface configured to receive a first medical image to which a first reconstruction parameter adapted to diagnose or analyze a first type of lesion is applied; and at least one processor configured to generate a second reconstruction parameter to be applied to the first medical image in response to a diagnosis order for the diagnosis or analysis of a second type of lesion. The at least one processor provides the second reconfiguration parameter to a user via a user interface, or generates a second medical image for the diagnose or analysis of the second type of lesion by executing the second reconstruction parameter on the first medical image and provides the second medical image to the user via the user interface.

The at least one processor may generate a second reconstruction parameter to be applied to the first medical image in response to a diagnosis order independently of a medical imaging device.

The at least one processor may be further configured to identify information about the first reconstruction parameter from the received information of the first medical image. The at least one processor may be further configured to transfer the information about the first reconstruction parameter and the diagnosis order to a first artificial neural network and to control the first artificial neural network to generate the second reconstruction parameter based on the information about the first reconstruction parameter and the diagnosis order.

The at least one processor may be further configured to transfer information about the first type of lesion, information about the second type of lesion, and the information about the first reconstruction parameter to the first artificial neural network. The at least one processor may be further configured to control the first artificial neural network to generate the second reconstruction parameter by converting the first reconstruction parameter based on the information about the first type of lesion, the information about the second type of lesion, and the information about the first reconstruction parameter.

The first artificial neural network may be an artificial neural network that has received a plurality of training datasets, including a first training reconstruction parameter derived to diagnose or analyze the first type of lesion for one original medical image and a second training reconstruction parameter derived to diagnose or analyze the second type of lesion for the original medical image. Furthermore, the first artificial neural network may be an artificial neural network that has learned the correlation between the first training reconstruction parameter and the second training reconstruction parameter corresponding to the correlation between the first type of lesion and the second type of lesion.

The computing system may further include a second artificial neural network configured to perform medical image analysis on the second medical image in response to the diagnosis order. The at least one processor may be further configured to input the second medical image to the second artificial neural network and to control the second artificial neural network so that the second artificial neural network generates a medical image analysis result for the second medical image. In this case, the medical image analysis of the first medical image may be executed by another artificial neural network inside the computing system or by still another artificial neural network outside the computing system.

According to an embodiment of the present invention, the computing system may further include a transmission interface configured to transmit data to the outside.

In this case, the at least one processor may be further configured to provide the second reconstruction parameter or the second medical image to a third artificial neural network via the transmission interface or the user interface in response to the diagnosis order. The at least one processor may be further configured to receive a medical image analysis result, obtained through inference in response to the diagnosis order by the third artificial neural network, via the receiver interface.

The diagnosis order may be determined based on a user command input from the user via the user interface, or may be determined based on predetermined information managed by the at least one processor and information about the first type of lesion.

The at least one processor may be further configured to provide 1) the results of the diagnosis or analysis of the first type of lesion performed on the first medical image, and 2) the results of the diagnosis or analysis of the second type of lesion performed on the second medical image together to the user via the user interface.

The at least one processor may be further configured to, when the user approves the second reconstruction parameter, store at least one of the second reconstruction parameter and the second medical image in a medical image database in association with the first medical image and the second reconstruction parameter. The medical image database may be a Picture Archive Communication System (PACS).

According to another aspect of the present invention, there is provided a medical image reconstruction apparatus for reconstructing a medical image to assist reading of a medical image based on a medical artificial neural network. The medical image reconstruction apparatus includes a computing system. The computing system includes: a receiver interface configured to receive a plurality of training datasets, including a first training reconstruction parameter derived to diagnose or analyze a first type of lesion for one original medical image, and a second training reconstruction parameter derived to diagnose or analyze a second type of lesion for the original medical image; at least one processor; and an artificial neural network.

The at least one processor may be further configured to transfer the plurality of training datasets to the artificial neural network and to control the artificial neural network to learn the correlation between the first training reconstruction parameter and the second training reconstruction parameter corresponding to the correlation between the first type of lesion and the second type of lesion.

According to still another aspect of the present invention, there is provided a medical image reconstruction method for reconstructing a medical image to assist reading of a medical image, the medical image reconstruction method being executed by a computing system. The computing system includes at least one processor. The medical image reconstruction method includes: receiving, by the at least one processor, a first medical image, to which a first reconstruction parameter adapted to diagnose or analyze a first type of lesion is applied, via a receiver interface; and generating, by the at least one processor, a second reconstruction parameter to be applied to the first medical image in response to a diagnosis order for the diagnosis or analysis of a second type of lesion.

The method further comprises providing, by the at least one processor, the second reconfiguration parameter to a user via a user interface. Or, the method further comprises generating, by the at least one processor, a second medical image for the diagnose or analysis of the second type of lesion by executing the second reconstruction parameter on the first medical image and providing, by the at least one processor, the second medical image to the user via the user interface.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
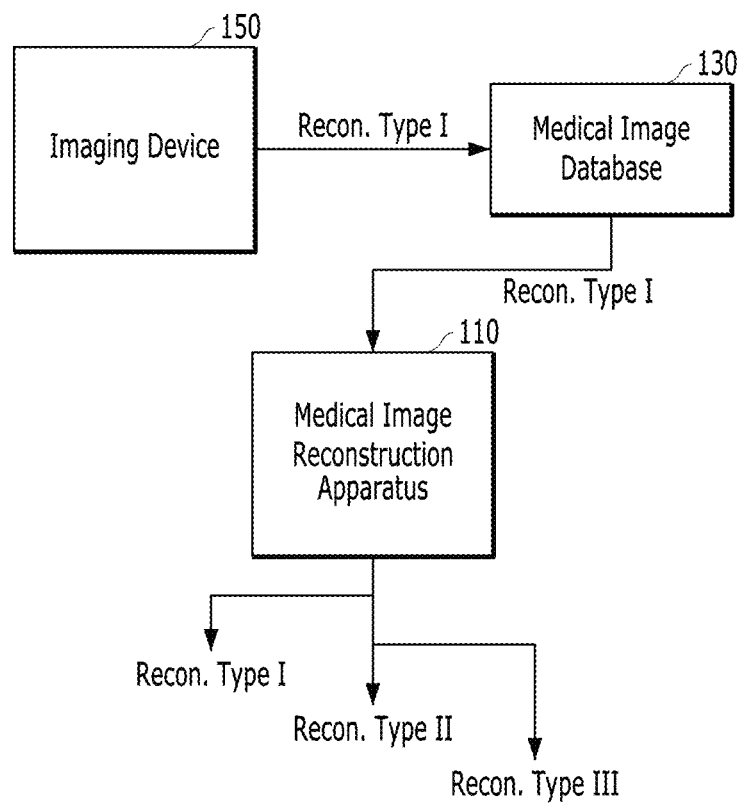
FIG. 1 is a diagram showing a workflow for performing medical image reconstruction and providing a plurality of medical image reconstruction parameters including a medical image reconstruction apparatus according to an embodiment of the present invention.

Objects other than the above-described objects and the features of the present invention will be apparent from the following description of embodiments to be given with reference to the accompanying drawings.

Embodiments of the present invention will be described in detail below with reference to the accompanying drawings. In the following description, when it is determined that a detailed description of a related known component or function may unnecessarily make the gist of the present invention obscure, it will be omitted.

Deep learning/CNN-based artificial neural network technology, which has recently developed rapidly, is considered for the purpose of identifying a visual element that is difficult to identify with the human eye when it is applied to the field of imaging. The fields of application of the above technology are expected to expand to various fields such as security, medical imaging, and non-destructive testing.

For example, in the field of medical imaging, there are cases where a tissue in question is not immediately diagnosed as a cancer tissue in a biopsy state but whether it is a cancer tissue is determined only after being monitored from a pathological point of view. Although it is difficult to confirm whether a corresponding cell is a cancer tissue in a medical image with the human eye, there is an expectation that the application of artificial neural network technology may acquire more accurate prediction results than observation with the human eye.

It is expected that this artificial neural network technology is applied to and performs the analysis process of detecting a disease or lesion that is difficult to identify with the human eye in a medical image, segmenting a region of interest such as a specific tissue, and measuring the segmented region.

A medical image can be used for the diagnosis of a disease or lesion only after going through the process of converting a set of signals, obtained from a medical imaging device such as a CT scanner, an MRI scanner, or an ultrasound scanner, into a state suitable for a medical professional to recognize. In this case, even for original data or an original medical image obtained from the same body part, a protocol for reconstructing a medical image varies depending on the type of disease/lesion to be diagnosed or detected.

The present invention provides a platform that can perform reconstruction into the most appropriate form for a human professional to read a specific disease/lesion using various analysis techniques for medical images. In this process, a more efficient reconstruction parameter (protocol) may be proposed using an artificial neural network (ANN).

In the related arts, when individual reconstruction parameters (protocols) are applied to original data or an original medical image, individual medical images capable of diagnosing a plurality of lesions, respectively, can be generated from the one original medical image. However, when a reconstruction process has been finished and a session has been completed in a medical imaging device, the original medical image is lost and a reconstruction process cannot be performed any longer.

The present invention can have excellent effects compared to the related arts at least in the following cases. Of course, it will be apparent to those skilled in the art from the disclosure of the present invention that the spirit of the present invention is not limited to the following examples.

For example, in the case where reconstruction parameter (protocol) A, reconstruction parameter (protocol) B, and reconstruction parameter (protocol) C capable of diagnosing/detecting/analyzing type A, type B, and type C diseases/lesions from one original medical image are present, when a diagnosis order for three types of diseases/lesions is given from the beginning, three versions of medical images will be generated with three reconstruction parameters (protocols) applied thereto, respectively. In general, it is much more frequent that only one or two reconfiguration parameters (protocols) are applied.

In this case, it is assumed that a doctor makes a preliminary diagnosis in which the possibility of a type A disease/lesion is highest through an interview between a patient and the doctor, only reconstruction parameter (protocol) A for the type A disease/lesion is executed, and only a version A medical image is generated. However, if, as a result of the actual analysis of the version A medical image, an analysis result suggests that the possibility of a type B or type C disease/lesion is higher than that of the type A disease/lesion, a new medical image needs to be generate in order to acquire a medical image for the type B or type C disease/lesion (because a medical imaging device has already completed a reconstruction session and an original medical image has been lost). There is a concern that such repetitive medical imaging exposes a patient to a higher radiation dose, which may harm the patient's health.

Accordingly, if the reconstruction parameter (protocol) B or reconstruction parameter (protocol) C capable of diagnosing/detecting/analyzing the type B or type C disease/lesion using only the version A medical image can be generated from reconstruction parameter (protocol) A through conversion, a medical image for the type B or type C disease/lesion may be acquired and the corresponding disease/lesion may be diagnosed/detected/analyzed without new medical imaging.

Alternatively, there may be assumed a case where in the case of a medical examination process, an examination applicant initially expresses his or her intention to examine herself or himself only for a type A disease/lesion and then expresses his/her intention to also examine herself or himself for type B and type C diseases/lesions after medical imaging. Alternatively, there may be assumed a case where after an examination applicant has initially expressed his/her intention to examine herself or himself only for a type A disease/lesion, medical staff reviews other statistics and/or information (e.g., other measurement/examination results, the possibility of another disease/lesion attributable to the lifestyle habits of the examination applicant, and/or the like) of the examination applicant and determines that there is a need to examine the examination applicant for the type B and type C diseases/lesions later after medical imaging.

Even in this case, reconstruction parameters (protocols) B and C may be derived from reconstruction parameter (protocol) A by using only the existing version A medical image without additional medical imaging through conversion, so that it may be possible to diagnose/detect/analyze the type B and C diseases/lesions based on the medical image while minimizing adverse effects on a patient or examination applicant.

The items known to those skilled in the art prior to the filing of the present application among the configuration of the present invention will be described as parts of the configuration of the present invention therein as necessary. However, when it is determined that the items obvious to those skilled in the art may make the gist of the invention obscure, descriptions thereof may be omitted. In addition, descriptions of the items omitted herein may be substituted by providing notification that they are known to those skilled in the art via the related art documents cited herein, e.g., U.S. Patent Application Publication No. US 2020/0335201 entitled "Method for Setting a Medical Imaging Protocol, System for Setting a Medical Instrument, Computer Program and Computer-Readable Medium," U.S. Patent Application Publication No. US 2020/0311490 entitled "Apparatus and Method for Sinogram Restoration in Computed Tomography (CT) Using Adaptive Filtering with Deep Learning (DL)," U.S. Pat. No. 10,565,477 entitled "Deep Learning Medical Systems and Methods for Image Reconstruction and Quality Evaluation," U.S. Patent Application Publication No. US 2019/0369191 entitled "MRI Reconstruction Using Deep Learning, Generative Adversarial Network and Acquisition Signal Model," and U.S. Patent Application Publication No. US 2020/0294284 entitled "Posterior Image Sampling Using Statistical Learning Model."

In U.S. Patent Application Publication No. US 2020/0311490 entitled "Apparatus and Method for Sinogram Restoration in Computed Tomography (CT) Using Adaptive Filtering with Deep Learning (DL)," there is disclosed the fact that the term "medical image reconstruction parameter (protocol)" refers to information about the parameter of a kernel or filter. The reconstruction protocol may refer to a sequence to which a plurality of parameters is applied according to the diagnosis purpose of a medical image or a diagnosis order.

Some of the items disclosed in these related art documents are related to the objects to be solved by the present invention, and some of the solutions adopted by the present invention are also applied to these related art documents.

In the following description to be given in conjunction with FIGS. 1 to 8, descriptions of the items considered to be well-known techniques that are widely known in the technical field of the present invention may be omitted as necessary in order to prevent the gist of the present invention from being obscured, or may be substituted by citing related art documents.

In addition, some or all of the configurations of the related art documents cited above and related art documents to be cited later may be related to some of the objects to be achieved by the present invention, and some of the solutions adopted by the present invention may be borrowed from the related art documents.

Only the items also included in order to embody the present invention among those disclosed in the related art documents will be considered to be parts of the configuration of the present invention.

Details of the present invention will be described below with reference to the embodiments of FIGS. 1 to 8.

FIG. 1 is a diagram showing a workflow for performing medical image reconstruction and providing a plurality of medical image reconstruction parameters including a medical image reconstruction apparatus 110 according to an embodiment of the present invention.

The medical image reconstruction apparatus 110 according to an embodiment of the present invention reconstructs a medical image in order to assist the reading of the medical image. A medical imaging device 150 generates a first medical image of reconstruction type I by applying and executing reconstruction parameter I based on the type/kind of a disease/lesion to be diagnosed. The first medical image generated by the medical imaging device 150 is stored in a medical image database 130, and may be transmitted from the medical image database 130 to the medical image reconstruction apparatus 110 in response to an invocation from the medical image reconstruction apparatus 110. In this case, the medical image database 130 may be a Picture Archive Communication System (PACS).

The medical image reconstruction apparatus 110 may generate a second reconstruction parameter and/or a third reconstruction parameter to be applied to the first medical image in response to a diagnosis order independently of the medical imaging device 150. The medical image reconstruction apparatus 110 may generate the second reconstruction parameter and/or the third reconstruction parameter to be applied to the first medical image by converting the first reconstruction parameter, and may generate the second medical image by applying the first reconstruction parameter to the first medical image. In this case, since a reconstruction session has already been finished in the medical imaging device 150, original medical image data has already been lost, and the additional reconstruction on the first medical image cannot be performed by the medical imaging device 150.

Figure 2:
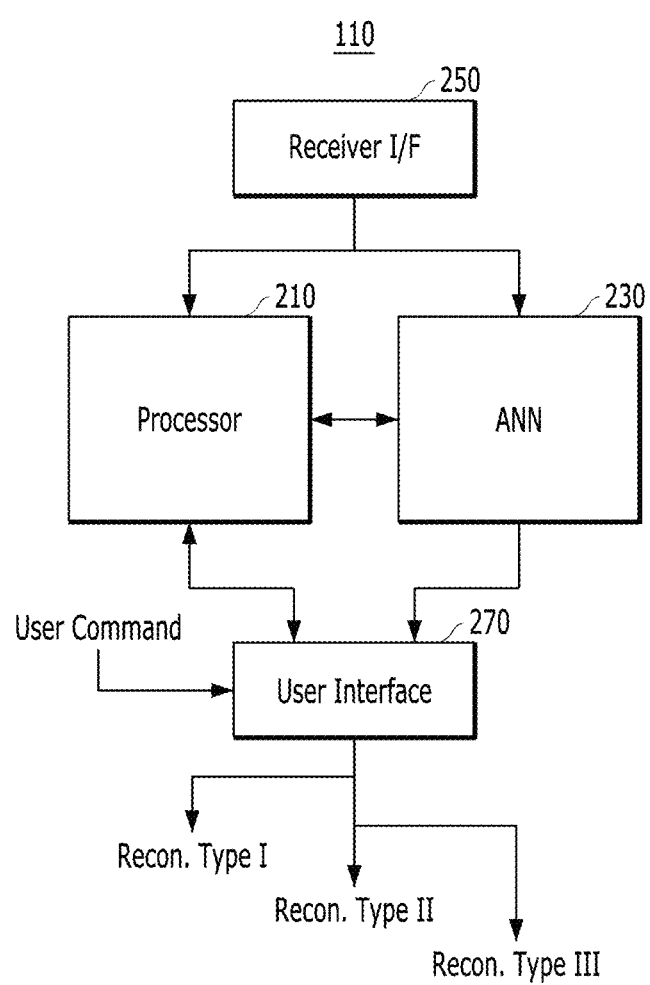
FIG. 2 is a block diagram showing an embodiment of the medical image reconstruction apparatus of FIG. 1.

FIG. 2 is a block diagram showing an embodiment of the medical image reconstruction apparatus 110 of FIG. 1.

Referring to FIG. 2, the medical image reconstruction apparatus 110 according to the present embodiment is an apparatus for reconstructing a medical image in order to assist the reading of the medical image, and may include a computing system (not shown). The computing system included in the medical image reconstruction apparatus 110 may include a receiver interface 250, at least one processor 210, and a first artificial neural network 230. In addition, the medical image reconstruction apparatus 110 may further include a user interface 270. Although not shown in FIG. 2, the medical image reconstruction apparatus 110 may further include a transmission interface configured to transmit data to the outside. The user interface 270 may include a display, a touch screen, a keyboard, a mouse, a trackball, a virtual keyboard, and so on.

Referring to FIGS. 1 and 2 together, the receiver interface 250 receives the first medical image to which a first reconstruction parameter adapted to diagnose or analyze a first type of lesion is applied. The at least one processor 210 generates a second reconstruction parameter to be applied to the first medical image in response to a diagnosis order for the diagnosis or analysis of a second type of lesion. When generating the second reconstruction parameter, the at least one processor 210 may generate the second reconstruction parameter by converting the first reconstruction parameter in cooperation with the first artificial neural network 230.

The at least one processor 210 may provide the second reconfiguration parameter to the user via the user interface 270. For example, the at least one processor 210 may provide information of the second reconfiguration parameter to the user via the display and the user may send the second reconfiguration parameter to another computing device to apply the second reconfiguration parameter to the first medical image and generate a second medical image. The user may approve, adjust, or modify the second reconfiguration parameter via the user interface 270 before applying it to the first medical image and/or sending it to the other computing device.

Otherwise, the at least one processor 210 may automatically and/or interactively generate a second medical image for the diagnosis or analysis of a second type of lesion by executing the second reconstruction parameter on the first medical image and provide the second medical image to the user via the user interface 270. In other words, an application having received the second reconstruction parameter via the user interface 270 may generate a second medical image by executing the second reconstruction parameter, or the second medical image may be generated within the medical image reconstruction apparatus 110 and then transferred to an external application via the user interface 270.

The at least one processor 210 may generate a second reconstruction parameter to be applied to the first medical image in response to a diagnosis order independently of the medical imaging device 150.

The diagnosis order may be determined based on a user command received from the user via the user interface 270. Alternatively, the diagnosis order may be determined based on predetermined information managed by the at least one processor 270 and information on the first type of lesion.

The at least one processor 210 may provide: 1) the results of the diagnosis or analysis of the first type of lesion performed on the first medical image; and 2) the results of the diagnosis or analysis of the second type of lesion performed on the second medical image together to the user via the user interface 270.

When the user approves at least one of the second reconstruction parameter and the second medical image, the at least one processor 210 may store at least one of the second reconstruction parameter and the second medical image in the medical image database 130 in association with the first medical image and the second reconstruction parameter. The medical image database 130 may be a PACS.

In this case, although the user may be a medical professional such as a clinician or a radiologist, the user may be an assistant staff member having only knowledge sufficient to check whether basic preprocessing such as image segmentation has been performed within a reasonable range depending on an object to be diagnosed. In other words, a person may approve the reconstruction parameters of the present invention and be included in the user meant in the present invention as long as the person does not have clinical knowledge but has a degree of representativeness sufficient to check whether main visual information for a specific diagnosis order has been appropriately represented by a corresponding reconstruction parameter.

The diagnosis order is an order indicating a disease/lesion to be diagnosed, and may be transferred through the medical information system or order communication system (OCS) of a hospital, and a diagnosis order for an additional disease/lesion may be generated according to predefined internal regulations. This may be the case where a patient or a person wishing to be examined wants to diagnose an additional disease/lesion or where a medical staff member acknowledges that the diagnosis of an additional disease/lesion is necessary.

When a user adds or selects a disease to be diagnosed, the process may be performed as follows. The user may check the kernel information of a currently given medical image and a diagnosis order suitable for diagnosis by a kernel via the user interface 270. When the user wants to add a new diagnosis order in addition to a given diagnosis order, he/she may add it via the user interface 270. The at least one processor 210 may perform kernel adaptation for a currently given kernel in order to derive a kernel that conforms to the new diagnosis order added by the user and is suitable for the diagnosis/detection/analysis of the disease/lesion of the new diagnosis order.

The at least one processor 210 may identify information about the first reconstruction parameter from the received information of the first medical image. The information about the first reconstruction parameter may be stored in the medical image database 130 together with the first medical image based on a DICOM standard.

Accordingly, the at least one processor 210 may identify the information about the first reconstruction parameter from the first medical image. The at least one processor 210 may transmit the information about the first reconstruction parameter and the diagnosis order to the first artificial neural network 230, and may control the first artificial neural network 230 so that the first artificial neural network 230 generates the second reconstruction parameter based on the information about the first reconstruction parameter and the diagnosis order.

The at least one processor 210 may transmit information about the first type/kind of lesion (or disease, tumor, malignant tissue, polyp, and so on), information about the second type/kind of lesion (or disease, tumor, malignant tissue, polyp, and so on), and information about the first reconstruction parameter to the first artificial neural network 230. The at least one processor 210 may control the first artificial neural network 230 so that the first artificial neural network 230 generates the second reconstruction parameter by converting the first reconstruction parameter based on the information about the first type/kind of lesion, the information about the second type/kind of lesion, and the information about the first reconstruction parameter. In this case, the conversion to the second reconstruction parameter (protocol) performed in the medical image reconstruction apparatus 110 of the present invention may be a type of kernel adaptation. The kernel adaptation between reconstruction parameters (protocols) will be performed on a pixel-to-pixel basis. When an artificial neural network is not used, it may be given in the form of a type of parameter relation. However, when the kernel adaptation is optimized pixel-wise, the amount of information will be huge, so that the information will be stored by a weighted dataset of an artificial neural network and constitute a learning model.

In this case, there are cases where some of the related arts use a generative adversarial neural network (GAN) or a conditional generative adversarial neural network (CGAN). However, since a GAN or CGAN does not entirely depend on an original medical image and generates a new image based on the original medical image, there is a risk that clinical characteristics included in the original medical image may be lost. The present invention does not use a GAN or CGAN, unlike the related arts, and the first artificial neural network 230 learns a kernel adaptation function and performs kernel adaptation based on a learned result weight dataset.

The first artificial neural network 230 may have received a plurality of training datasets, including a first training reconstruction parameter derived to diagnose or analyze a first type/kind of lesion for one original medical image and a second training reconstruction parameter derived to diagnose or analyze a second type/kind of lesion for the original medical image. The first artificial neural network 230 may have learned the correlation between the first training reconstruction parameter and the first type/kind lesion and the correlation between the second training reconstruction parameter and the second type/kind lesion. Furthermore, the first artificial neural network 230 may be an artificial neural network that has learned the correlation between the first training reconstruction parameter and the second training reconstruction parameter corresponding to the correlation between the first type/kind of lesion and the second type/kind of lesion.

The computing system may further include a second artificial neural network (not shown) that performs medical image analysis on the second medical image in response to the diagnosis order. The at least one processor 210 may input the second medical image to the second artificial neural network, and may control the second artificial neural network so that the second artificial neural network generates a medical image analysis result for the second medical image. In this case, the medical image analysis of the first medical image may be executed by another artificial neural network inside the computing system or by still another artificial neural network outside the computing system.

In the embodiments shown in FIGS. 1 and 2, the medical image reconstruction apparatus 110 may convert the first reconstruction parameter into the second reconstruction parameter in order to generate the second reconstruction parameter, and kernel adaptation may generate a kernel suitable for the diagnosis/detection/analysis of the second type/kind of lesion included in the new diagnosis order as the second reconstruction parameter without taking into consideration the first reconstruction parameter. The process of selecting a kernel suitable for the performance of the task of a new diagnosis order will be described later with reference to FIGS. 3 to 8.

Figure 3:
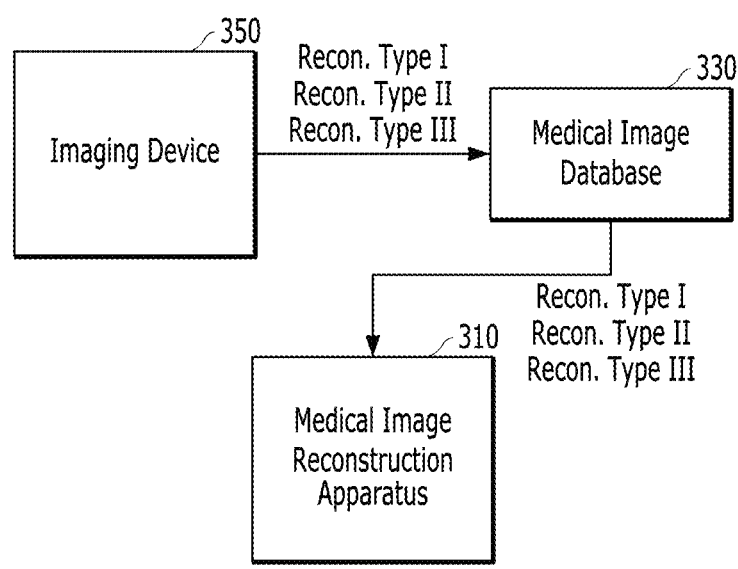
FIG. 3 is a diagram showing a training process in which a medical image reconstruction apparatus learns the function of generating a reconstruction protocol according to an embodiment of the present invention.

FIG. 3 is a diagram showing a training process in which the medical image reconstruction apparatus 310 learns the function of generating a reconstruction parameter according to an embodiment of the present invention.

The medical image reconstruction apparatus 310 according to an embodiment of the present invention may reconstruct a medical image in order to assist the reading of the medical image based on a medical artificial neural network. The medical image reconstruction apparatus includes a computing system. The computing system may receive a plurality of training datasets, including a first training reconstruction parameter derived to diagnose or analyze a first type of lesion for one original medical image and a second training reconstruction parameter derived to diagnose or analyze a second type of lesion for the original medical image.

The medical imaging device 350 shown in FIG. 3 may generate a first training medical image, a second training medical image, and a third training medical image by applying and executing a first training reconstruction parameter, a second training reconstruction parameter, and a third training reconstruction parameter onto one original medical image. The first training medical image, the second training medical image, and the third training medical image generated by the medical imaging device 350 may be stored in the medical image database 330, and may be transferred to the medical image reconstruction apparatus 310 in response to a request from the medical image reconstruction apparatus 310.

Figure 4:
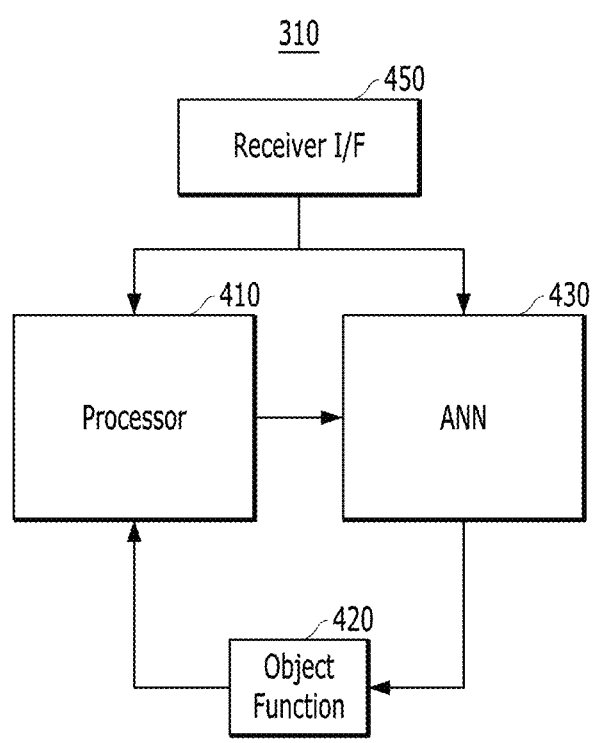
FIG. 4 is a block diagram showing a training/learning process executed inside the medical image reconstruction apparatus of FIG. 3.

FIG. 4 is a block diagram showing a training/learning process executed inside the medical image reconstruction apparatus 310 of FIG. 3.

The medical image reconstruction apparatus 310 includes a receiver interface 450 configured to receive a first medical training image, a second training medical image, and a third training medical image generated for one original medical image, at least one processor 410, and an artificial neural network 430. Reconstruction parameters contributing to the generation of the individual training medical images are stored in the medical image database 330 based on a medical image standard. In this case, the medical image database 330 may be a system based on a standard such as a PACS.

The medical image reconstruction parameter (protocol) encompasses information required to re-visualize a medical image in a user viewer, and may include all of the following information. In the PACS, conditions used when imaging or generating a medical image, i.e., a dose, kernel information used, and vendor-related information, are specified and stored together with the medical image. Furthermore, a diagnosis order on which each medical image is generated based, i.e., information about a disease/lesion to be diagnosed using the corresponding medical image, may also be stored in the PACS together with the medical image.

The at least one processor 410 transfers a plurality of training datasets to the artificial neural network 430, and controls the artificial neural network 430 so that the artificial neural network 430 learns the correlation between the first training reconstruction parameter and the second training reconstruction parameter corresponding to the correlation between the first type of lesion and the second type of lesion.

The artificial neural network 430 may identify a plurality of reconstruction parameters derived from the same original medical image, and may learn the correlation between the reconstruction parameters. In this case, since each reconstruction parameter includes a diagnosis order to be diagnosed, the artificial neural network 430 may learn the correlation between the first training reconstruction parameter derived to diagnose or analyze the first type of lesion from the same original medical image and the second training reconstruction parameter derived to diagnose or analyze the second type of lesion from the same original medical image based on the correlation between the first type of lesion and the second type of lesion. This training dataset is transferred to the artificial neural network 430 with a diagnosis order (disease/lesion) and a reconstruction parameter separated for each of a plurality of original medical images, and the artificial neural network 430 may learn the function of converting the first reconstruction parameter for the first type of lesion into the second reconstruction parameter for the second type of lesion and the function of converting the second reconstruction parameter for the second type of lesion into the first reconstruction parameter for the first type of lesion.

Meanwhile, in this case, the training dataset used for training is limited to the case where it is approved by the user as a reconfiguration parameter that is appropriately generated in response to a specific diagnosis order, and the quality of a training dataset may be improved when the training dataset goes through this approval process.

In the artificial neural network 430, temporary reconstruction parameters generated in a training process through an objective function 420 are fed back to reduce errors with reference protocols given as training data. As training is repeated, the artificial neural network 430 learns the function to generate reconstruction parameters equivalent to the reference protocols.

Figure 5:
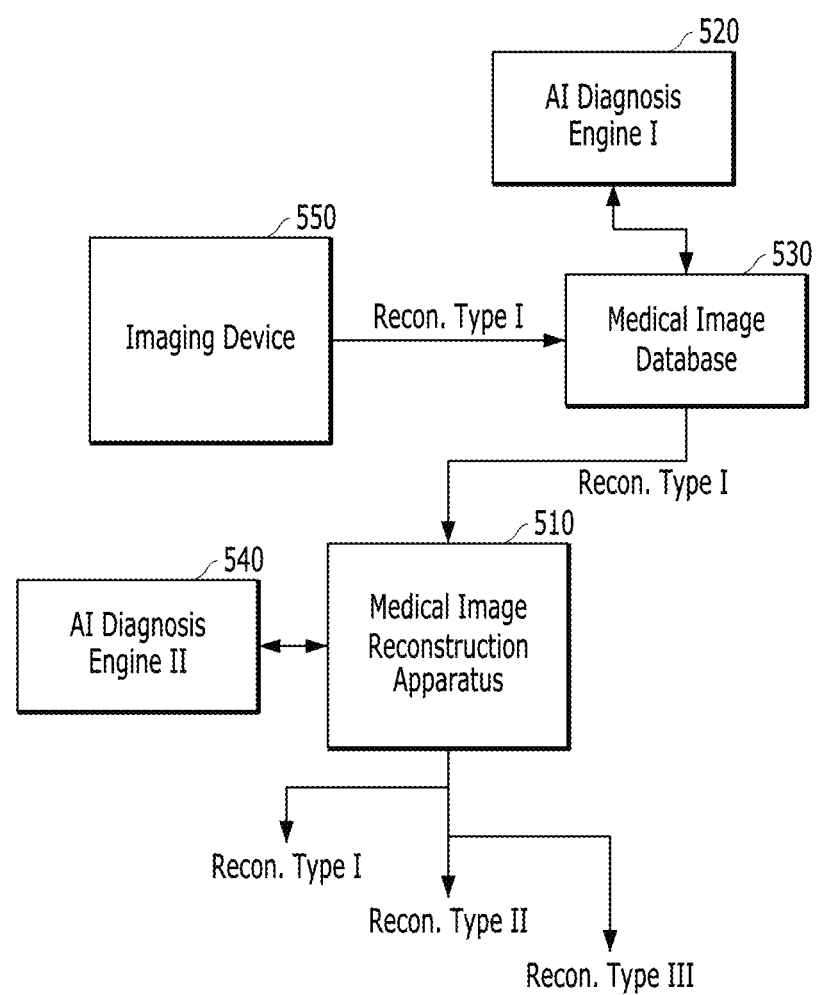
FIG. 5 is a diagram showing a workflow for performing medical image reconstructing and providing a plurality of medical image reconstruction parameters including a medical image reconstruction apparatus according to an embodiment of the present invention.

FIG. 5 is a diagram showing a workflow for performing medical image reconstruction and providing a plurality of medical image reconstruction parameters including a medical image reconstruction apparatus 510 according to an embodiment of the present invention.

Since the operations of the medical imaging device 550 and medical image database 530 of FIG. 5 are considerably similar to those of the medical imaging device 110 and medical image database 130 of FIG. 1, redundant descriptions thereof will be omitted.

According to an embodiment of the present invention, the medical image reconstruction apparatus 510 may further include a transmission interface (not shown) configured to transmit data to the outside. In this case, the at least one processor of the medical image reconstruction apparatus 510 may provide a second reconstruction parameter or a second medical image to a third artificial neural network 540 in response to a diagnosis order via the transmission interface or a user interface. The at least one processor may receive the result of medical image analysis performed in response to a diagnosis order by the third artificial neural network 540 via a receiver interface.

Furthermore, the process of diagnosing/detecting/analyzing a first type of lesion using a first medical image may be performed by another fourth artificial neural network 520 outside the medical image reconstruction apparatus 510 of FIG. 5.

Although the embodiments in which the medical image database 130, 330, or 530 is located outside are shown in FIGS. 1 to 5, it will be apparent to those skilled in the art that according to another embodiment of the present invention, an embodiment in which a database (not shown) is located inside the medical image reconstruction apparatus 110, 310, or 510 may also be implemented.

Figure 6:
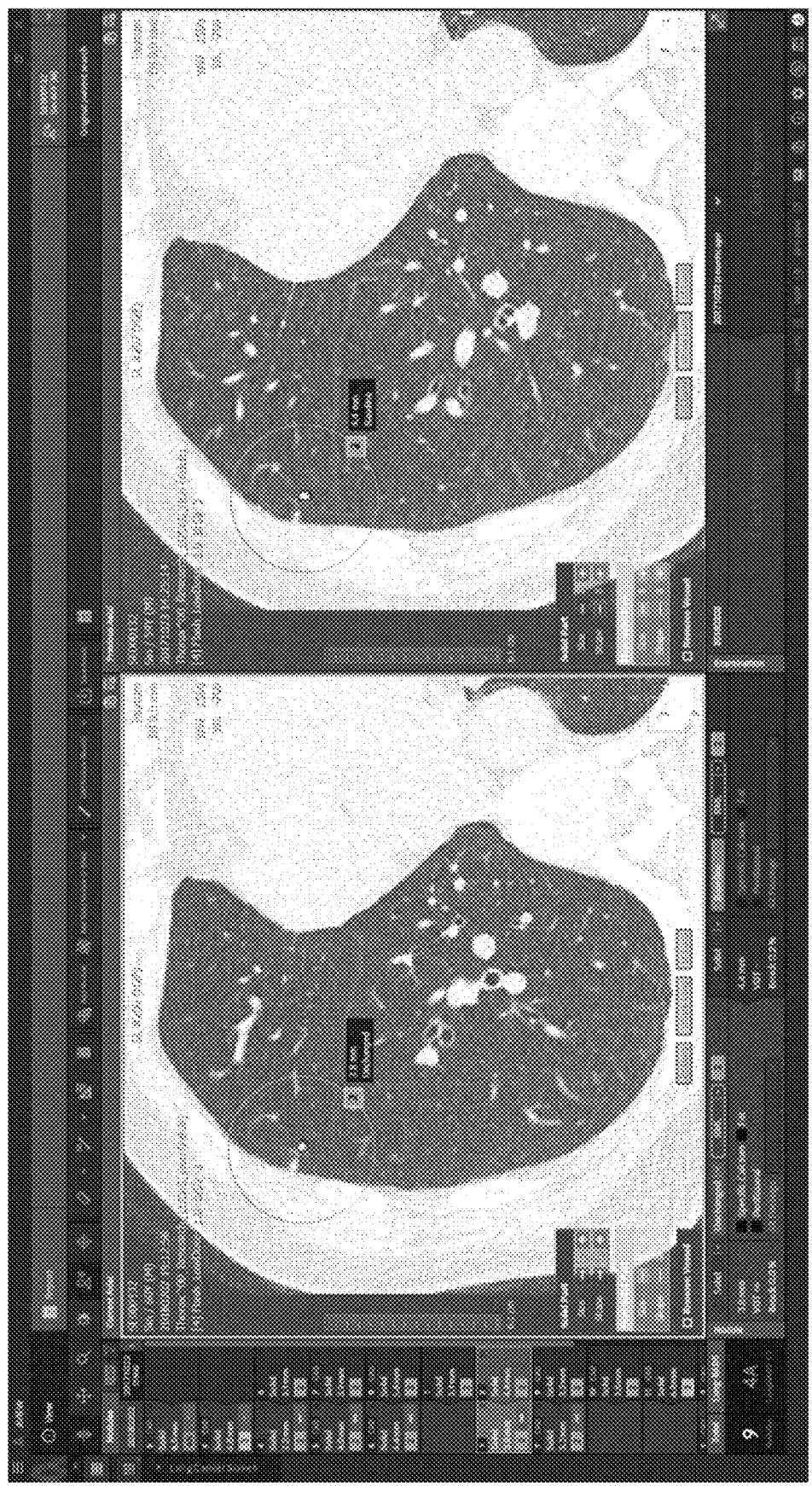
FIG. 6 shows an example of medical image reconstruction parameters according to an embodiment of the present invention, which is an example of medical image reconstruction parameters and a medical image diagnosis/analysis screenshot for lung cancer screening (LCS)

FIG. 6 shows an example of medical image reconstruction parameters according to an embodiment of the present invention, which is an example of medical image reconstruction parameters and a medical image diagnosis/analysis screenshot for lung cancer screening (LCS).

The lung cancer screening shown in FIG. 6 is used to detect lung nodules after reconstruction based on a high frequency or a sharp kernel when performed on a low-dose or ultralow-dose CT. Although various conventional techniques have been proposed for this, it is most important to distinguish between a normal organ and a lesion, and thus it is an important goal to derive a region having a brightness value different from a surrounding brightness.

Figure 7:
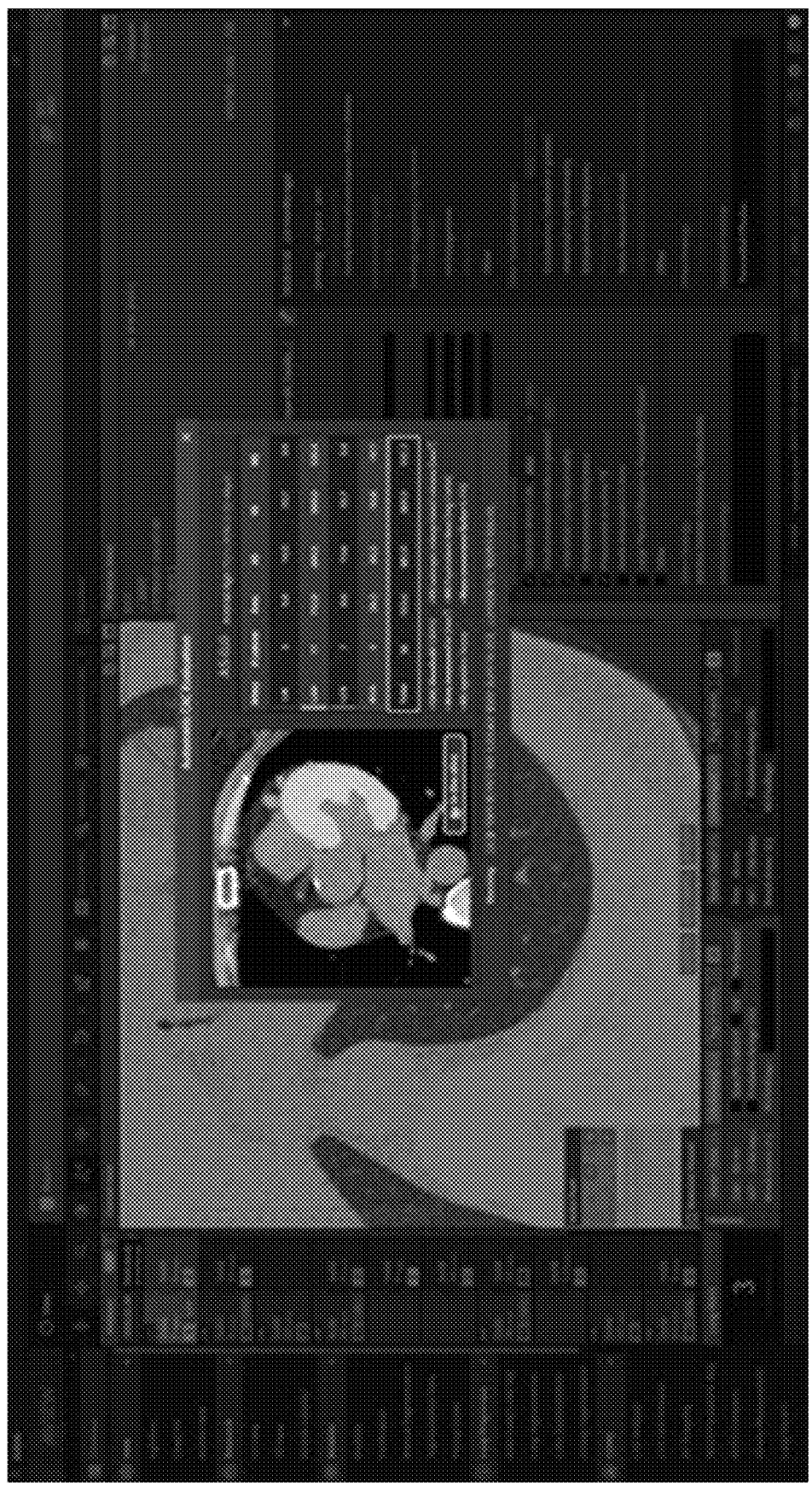
FIG. 7 shows an example of medical image reconstruction protocols according to an embodiment of the present invention, which is an example of image reconstruction parameters and a corresponding medical image diagnosis/analysis screenshot for coronary artery calcification (CAC) scoring based on the medical images of FIG. 6 received for lung cancer screening.

FIG. 7 shows an example of medical image reconstruction protocols according to an embodiment of the present invention, which is an example of image reconstruction parameters and a corresponding medical image diagnosis/analysis screenshot for coronary artery calcification (CAC) scoring based on the medical images of FIG. 6 received for lung cancer screening.

Referring to FIG. 7, an image reconstructed by applying a soft kernel to an image to which a sharp kernel has been applied and which is received for LCS screening is shown. Furthermore, an image visualized by applying a CAC scoring algorithm to the reconstructed image is overlaid and shown.

The golden rule for CAC scoring is to perform analysis using ECG-gated CT images. However, it has been reported that when a standard kernel or soft kernel is applied to low-dose CT, the result of CAC scoring even in the case where an original image is a non-gated image does not show a significant difference from that in the case where an ECG-gated CT image is used. Of course, in this case, the result of the CAC scoring of the image reconstructed by applying the soft kernel to the non-gated CT image is not completely reliable.

However, it is recognized that the relevance thereof is sufficient to be used as a means of screening whether a patient requires detailed CAC analysis.

The results of CAC scoring shown in FIG. 7 are somewhat different from those in a method of directly detecting a calcium region in the related art. In this case, when a diagnosis order is CAC scoring, a cardiovascular segmentation process is executed as a preprocessing process. In this case, when there is an error in the cardiovascular segmentation process and thus a rib region is incorporated into a vascular region, there may occur an error in which a CAC store may be measured as considerably larger than an actual value. Accordingly, through the consideration of this error, there may be visualized one image in which all the calcified regions detected on an axial image are displayed. Thereafter, bright and dark regions are distinguished from each other by thresholding the cardiovascular region.

For the simple detection of coronary artery calcification, there may be cases where a sharp kernel applied for LCS is more advantageous. However, when the configuration of quantifying and comparing bright and dark parts after segmentation is regarded as important, a soft kernel may appear more effective. In other words, the results of kernel adaptation may vary depending on specific medical image analysis and visualization methods as well as a diagnosis order. In order to provide kernel adaptation optimized by taking into consideration this variation, it is necessary for a user to check each analysis and visualization result and to approve the optimized kernel, thereby increasing the accuracy and reliability of a training dataset.

Figure 8:
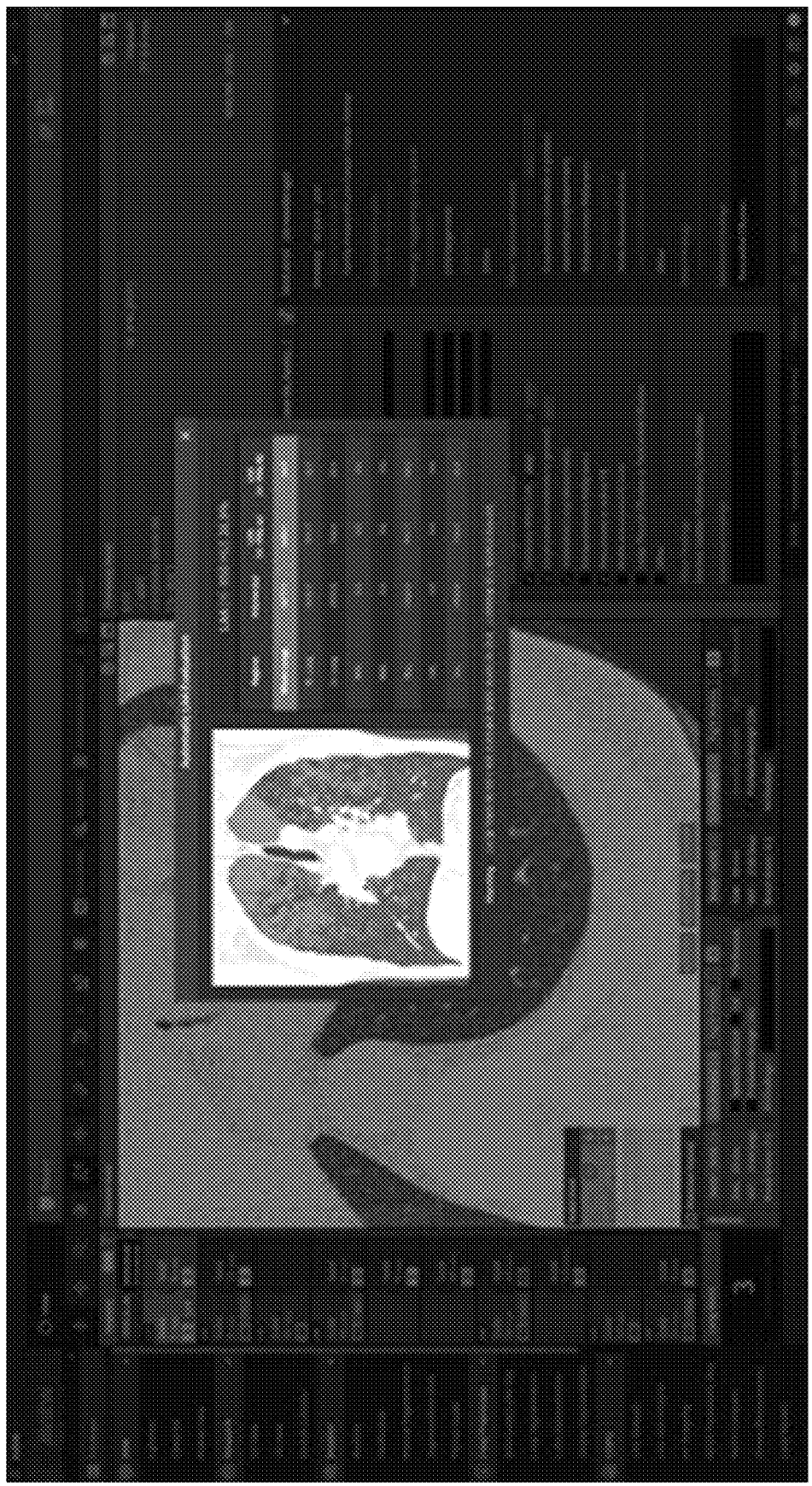
FIG. 8 shows an example of medical image reconstruction protocols according to an embodiment of the present invention, which is an example of medical image reconstruction protocols and a corresponding medical image diagnosis/analysis screenshot for diagnosing emphysema or chronic obstructive pulmonary disease (COPD) by measuring/analyzing an emphysema index based on the medical images of FIG. 6 received for lung cancer screening.

FIG. 8 shows an example of medical image reconstruction parameters according to an embodiment of the present invention, which is an example of medical image reconstruction parameters and a corresponding medical image diagnosis/analysis screenshot for diagnosing chronic obstructive pulmonary disease (COPD) and emphysema by measuring/analyzing an emphysema index based on the medical images of FIG. 6 received for lung cancer screening.

Referring to FIG. 8, the results of the analysis of the medical image that quantify low attenuation areas (LAAs) by thresholding bright and dark parts in a lung area are displayed together with the results of the kernel adaptation of the medical image.

Although a sharp kernel may be suitable for a case where emphysema is simply detected to diagnose COPD, a soft kernel tends to be more suitable than a sharp kernel for quantifying LAAs. In this case, the kernel that is suitable for diagnosing/analyzing/detecting a specific type of lesion may be determined by comparing the results of the automatic diagnosis/analysis/detection of a corresponding type of lesion after the application of different kernels, the results of the diagnosis/analysis/detection of the corresponding type of lesion performed by a medical professional after the application of different kernels, and/or the results of the diagnosis/analysis/detection of the corresponding type of lesion verified through an actual biopsy. The kernel that derives results having the highest reliability and accuracy via the peer review of the results of the diagnosis/analysis/detection of the corresponding type of lesion performed by a medical professional may be evaluated as the most appropriate kernel.

Accordingly, as shown in FIG. 8, a medical image reconstructed by applying a soft kernel different from the medical image reconstruction parameter of FIG. 6 is displayed, and LAA analysis is performed based on the reconstructed image and then emphysema quantitative analysis results for COPD diagnosis are overlaid and displayed.

A low attenuation area (LAA) is a result of the analysis of a CT image including the lungs, and may refer to a region in which a brightness value in a CT image is lower than a reference value. In normal alveoli, the brightness value in the CT image may vary according to the phase of respiration. However, in the CT image of the lungs, a region in which a brightness value less than a specific reference value is continuously maintained is an image filled with air, and is considered to have ruptured or inactivated alveoli, so that it may be determined to be a region not conducive to breathing.

The quantitative analysis results for LAAs may be represented by the ratio of the volume of regions, in which a brightness value is maintained below the reference value (e.g., −950 HU) within a specific area, to the volume of the corresponding area. Another quantitative analysis results for LAAs may also be represented by classifying the sizes of LAAs and counting and displaying the number of LAAs for each size. These quantification results vary depending on a patient's respiration level (how much breath is inhaled). When the quantification results are processed using a log operation, a constant value independent of the respiration level is derived, and may be provided as an index for the patient's overall lung capacity. The quantitative measurement results for the LAAs are provided to the user for the diagnosis of chronic obstructive pulmonary disease (COPD), etc., and may assist the diagnosis.

The LAA analysis results are obtained through a plurality of image processing steps.

A lung CT image may be segmented into a whole lung, a left lung, and a right lung. Each of the left lung and the right lung may be divided into lung lobes.

The reference area for deriving the ratio of LAAs for each area from the LAA analysis results may be a lung lobe obtained as described above or the left or right lung.

If there are errors in a plurality of preprocessing steps necessary to derive the LAA analysis results, the reliability of the LAA analysis results may also be deteriorated.

Therefore, based on the analysis results, the preprocessing results of the plurality of preprocessing processes used to obtain analysis results may be visualized along with a representative visualization form and then provided together with the analysis results.

The medical image reconstruction method according to an embodiment of the present invention is a medical image reconstruction method for reconstructing a medical image to assist the reading of a medical image executed by a computing system, and the computing system includes at least one processor.

The medical image reconstruction method according to an embodiment of the present invention may be loaded into memory in the form of program instructions and invoked and executed by a processor, a controller, and/or electronic circuit logic designed in a distributed manner.

For example, the process in which the at least one processor 210 disclosed in FIG. 2 receives a first medical image, to which a first reconstruction parameter adapted to diagnose or analyze a first type of lesion is applied, via the receiver interface 250 may be implemented in the form of program instructions and executed as the step of receiving the first medical image.

Furthermore, the process in which the at least one processor 210 generates a second reconstruction parameter to be applied to a first medical image in response to a diagnosis order for the diagnosis or analysis of a second type of lesion may also be implemented in the form of program instructions and executed as the step of generating the second reconfiguration parameter. In this case, after the second reconstruction parameter having high relevance to the second type of lesion corresponding to the diagnosis order has been selected, it may be determined whether the first reconstruction parameter already applied to the first medical image and completed is the same as the second reconstruction parameter. In an embodiment, when the first reconstruction parameter is the same as the second reconstruction parameter, the first medical image may be provided in response to the diagnosis order for the diagnosis or analysis of the second type of lesion without reconstructing the first medical image. In contrast, when the first reconstruction parameter is different from the second reconstruction parameter, the second reconstruction parameter may be selected as a reconstruction parameter to be applied to the first medical image in response to the diagnosis order corresponding to the second type of lesion.

The process in which the at least one processor 210 provides the second reconstruction parameter to the user via the user interface 270, or generates a second medical image for the diagnosis or analysis of the second type of lesion by executing the second reconstruction parameter for the first medical image and provides the second medical image to the user via the user interface 270 may be implemented in the form of program instructions and executed as the step of providing the second reconstruction parameter or the second medical image to the user.

According to the present invention, there may be proposed a new reconstruction parameter and/or reconstruction protocol suitable for diagnosing/analyzing an additional disease or lesion without damaging the clinical characteristics of an original medical image from a medical image received after a reconstruction process has already been completed in a medical imaging device. According to the present invention, a new medical image may be reconstructed based on the new reconstruction parameter and/or reconstruction protocol, and the additional disease or lesion may be diagnosed/analyzed.

According to the medical image reconstruction apparatus and method of the present invention, an additional disease or lesion may be diagnosed/analyzed from a currently given medical image by executing medical image processing via software independently from a medical imaging device.

According to the present invention, there may be implemented the technique for conversion between medical image reconstruction parameters (protocols) capable of diagnosing/analyzing an additional disease or lesion from the same original medical image by using the training/learning and inference of the artificial neural network. In this case, the conversion between medical image reconstruction parameters (protocols) is performed independently of the medical imaging device, and may be performed even in an environment in which information about an original medical image cannot be received from the medical imaging device because the medical imaging device finishes a medical image reconstruction process.

The method according to an embodiment of the present invention may be implemented in the form of program instructions executable by a variety of computing means and then recorded in a computer-readable storage medium. The computer-readable storage medium may include program instructions, data files, and data structures solely or in combination. Program instructions recorded in the storage medium may have been specially designed and configured for the present invention, or may be known to or available to those who have ordinary knowledge in the field of computer software. Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

However, the present invention is not limited to the embodiments. Like reference symbols in the drawings designate like components. The lengths, heights, sizes, widths, etc. introduced in the embodiments and drawings of the present invention may be exaggerated to help to understand the present invention.

Although the present invention has been described with reference to specific details such as the specific components, and the limited embodiments and drawings, these are provided merely to help a general understanding of the present invention, and the present invention is not limited thereto. Furthermore, those having ordinary skill in the art to which the present invention pertains may make various modifications and variations from the above detailed description.

Therefore, the spirit of the present invention should not be defined based only on the described embodiments, and not only the attached claims but also all equivalents to the claims should be construed as falling within the scope of the spirit of the present invention.

What is claimed is:

1. A medical image reconstruction apparatus for reconstructing a medical image to assist reading of a medical image, the medical image reconstruction apparatus comprising a computing system, wherein the computing system comprises:
a receiver interface configured to receive a first medical image to which a first reconstruction parameter adapted to diagnose or analyze a first type of lesion is applied; and
at least one processor configured to:
transfer a diagnosis order for a diagnosis or analysis of a second type of lesion to a first artificial neural network; and
control the first artificial neural network to generate a second reconstruction parameter to be applied to the first medical image in response to the diagnosis order,
wherein the at least one processor provides the second reconfiguration parameter to a user via a user interface, or generates a second medical image for a diagnose or analysis of the second type of lesion by executing the second reconstruction parameter on the first medical image and provides the second medical image to the user via the user interface.

2. The medical image reconstruction apparatus of claim 1, wherein the at least one processor is further configured to:
identify information about the first reconstruction parameter from received information of the first medical image;
transfer the information about the first reconstruction parameter and the diagnosis order to the first artificial neural network; and
control the first artificial neural network to generate the second reconstruction parameter based on the information about the first reconstruction parameter and the diagnosis order.

3. The medical image reconstruction apparatus of claim 2, wherein the at least one processor is further configured to:
transfer information about the first type of lesion, information about the second type of lesion, and the information about the first reconstruction parameter to the first artificial neural network; and
control the first artificial neural network to generate the second reconstruction parameter by converting the first reconstruction parameter based on the information about the first type of lesion, the information about the second type of lesion, and the information about the first reconstruction parameter.

4. The medical image reconstruction apparatus of claim 2, wherein the first artificial neural network is an artificial neural network that has received a plurality of training datasets, including a first training reconstruction parameter derived to diagnose or analyze the first type of lesion for one original medical image and a second training reconstruction parameter derived to diagnose or analyze the second type of lesion for the original medical image, and that has learned a correlation between the first training reconstruction parameter and the second training reconstruction parameter corresponding to a correlation between the first type of lesion and the second type of lesion.

5. The medical image reconstruction apparatus of claim 2, wherein the computing system further comprises a second artificial neural network configured to perform medical image analysis on the second medical image in response to the diagnosis order, and
wherein the at least one processor is further configured to input the second medical image to the second artificial neural network and control the second artificial neural network to generate a medical image analysis result for the second medical image.

6. The medical image reconstruction apparatus of claim 1, wherein the at least one processor is further configured to:
provide the second reconstruction parameter or the second medical image to a third artificial neural network via a transmission interface or the user interface in response to the diagnosis order; and
receive a medical image analysis result, obtained through inference in response to the diagnosis order by the third artificial neural network, via the receiver interface.

7. The medical image reconstruction apparatus of claim 1, wherein the diagnosis order is determined based on a user command input from the user via the user interface, or is determined based on predetermined information managed by the at least one processor and information about the first type of lesion.

8. The medical image reconstruction apparatus of claim 1, wherein the at least one processor is further configured to provide:
results of the diagnosis or analysis of the first type of lesion performed on the first medical image; and
results of the diagnosis or analysis of the second type of lesion performed on the second medical image,
together to the user via the user interface.

9. The medical image reconstruction apparatus of claim 1, wherein the at least one processor is further configured to, when the user approves the second reconstruction parameter, store at least one of the second reconstruction parameter and the second medical image in a medical image database in association with the first medical image and the second reconstruction parameter.

10. A medical image reconstruction apparatus for reconstructing a medical image to assist reading of a medical image based on a medical artificial neural network, the medical image reconstruction apparatus comprising a computing system, wherein the computing system comprises:
a receiver interface configured to receive a plurality of training datasets, including a first training reconstruction parameter derived to diagnose or analyze a first type of lesion for one original medical image, and a second training reconstruction parameter derived to diagnose or analyze a second type of lesion for the original medical image;
at least one processor; and
an artificial neural network,
wherein the at least one processor is configured to:
transfer the plurality of training datasets to the artificial neural network; and
control the artificial neural network to learn a correlation between the first training reconstruction parameter and the second training reconstruction parameter corresponding to a correlation between the first type of lesion and the second type of lesion.

11. A medical image reconstruction method for reconstructing a medical image to assist reading of a medical image, the medical image reconstruction method being executed by a computing system, the computing system comprising at least one processor and a receiver interface, the medical image reconstruction method comprising:
receiving, by the at least one processor, a first medical image, to which a first reconstruction parameter adapted to diagnose or analyze a first type of lesion is applied, via the receiver interface;

transferring, by the at least one processor, a diagnosis order for a diagnosis or analysis of a second type of lesion to a first artificial neural network; and controlling, by the at least one processor, the first artificial neural network to generate a second medical image adapted to diagnose or analyze the second type of lesion by reconstructing the first medical image or a second reconstruction parameter to be applied to the first medical image for generating the second medical image in response to the diagnosis order.

12. The medical image reconstruction method of claim 11, further comprising:
providing, by the at least one processor, the second reconfiguration parameter to a user via a user interface.

13. The medical image reconstruction method of claim 11, further comprising:
generating, by the at least one processor, a the second medical image for a diagnose or analysis of the second type of lesion by executing the second reconstruction parameter on the first medical image and providing, by the at least one processor, the second medical image to the user via the user interface.

14. The medical image reconstruction method of claim 11, further comprising:
identifying, by the at least one processor, information about the first reconstruction parameter from received information of the first medical image;
transferring, by the at least one processor, the information about the first reconstruction parameter and the diagnosis order to the first artificial neural network; and
controlling, by the at least one processor, the first artificial neural network to generate the second reconstruction parameter based on the information about the first reconstruction parameter and the diagnosis order.

15. The medical image reconstruction method of claim 14, further comprising:
inputting, by the at least one processor, the second medical image by executing the second reconstruction parameter on the first medical image, to the second artificial neural network configured to analyze the second medical image in response to the diagnosis order; and
controlling, by the at least one processor, the second artificial neural network to generate a medical image analysis result for the second medical image.

16. The medical image reconstruction method of claim 11, further comprising:
providing, by the at least one processor, the second reconstruction parameter or a-the second medical image by executing the second reconstruction parameter on the first medical image, to a third artificial neural network via a transmission interface or the user interface in response to the diagnosis order; and
receiving, by the at least one processor, a medical image analysis result, obtained through inference in response to the diagnosis order by the third artificial neural network, via the receiver interface.

17. The medical image reconstruction method of claim 11, further comprising providing, by the at least one processor:
results of the diagnosis or analysis of the first type of lesion performed on the first medical image; and
results of the diagnosis or analysis of the second type of lesion performed on the second medical image,
together to the user via the user interface.

18. The medical image reconstruction method of claim 11, further comprising:
when the user approves the second reconstruction parameter, storing, by the at least one processor, at least one of the second reconstruction parameter and the second medical image in a medical image database in association with the first medical image and the second reconstruction parameter.

19. A medical image reconstruction apparatus for reconstructing a medical image to assist reading of a medical image, the medical image reconstruction apparatus comprising a computing system, wherein the computing system comprises:
a receiver interface configured to receive a first medical image adapted to diagnose or analyze a first type of lesion is applied; and
at least one processor configured to:
transfer a diagnosis order for a diagnosis or analysis of a second type of lesion to an artificial neural network; and
control the artificial neural network to generate a second medical image adapted to diagnose or analyze the second type of lesion by reconstructing the first medical image in response to the diagnosis order; and
provide the second medical image to a user via a user interface.

20. The medical image reconstruction method of claim 19, wherein a first reconstruction parameter adapted to diagnose or analyze a first type of lesion is applied to the first medical image, and
wherein the at least one processor is further configured to control the artificial neural network to generate the second medical image by applying a second reconstruction parameter adapted to diagnose or analyze the second type of lesion to reconstruct the first medical image.

* * * * *